US00PP27338P2

(12) United States Plant Patent
Wain

(10) Patent No.: US PP27,338 P2
(45) Date of Patent: Nov. 1, 2016

(54) ***CHRYSANTHEMUM* PLANT NAMED 'FIMMEVENYEL'**

(50) Latin Name: *Chrysanthemum×morifolium*
Varietal Denomination: Fimmevenyel

(71) Applicant: Peter Wain, Locks Heath (GB)

(72) Inventor: Peter Wain, Locks Heath (GB)

(73) Assignee: Fides B.V., De Lier (NL)

( * ) Notice: Subject to any disclaimer, the term of this patent is extended or adjusted under 35 U.S.C. 154(b) by 89 days.

(21) Appl. No.: 14/121,721

(22) Filed: Oct. 11, 2014

(51) Int. Cl.
*A01H 5/02* (2006.01)

(52) U.S. Cl.
USPC ..... Plt./289
CPC ..... *A01H 5/0255* (2013.01)

(58) Field of Classification Search
USPC ..... Plt./289
See application file for complete search history.

(56) References Cited

PUBLICATIONS

Dummen Orange 2015-2016, retrieved on Mar. 3, 2016, retrieved from the Internet at <http://dummenorange.com/wp-content/uploads/2015/12/Pot-plants-Europe-EN-DE-NL.pdf> pp. 1-3 and 46.*
Turks' Greenhouses Mums 2014 retrieved on Mar. 3, 2016, retrieved from the Internet at <http://www.turksgreenhouses.com/downloads-files/fall%20brochure%202014%201st%20edition.pdf> 8 pp.*

* cited by examiner

*Primary Examiner* — June Hwu
(74) *Attorney, Agent, or Firm* — C. A. Whealy

(57) ABSTRACT

A new and distinct cultivar of *Chrysanthemum* plant named 'Fimmevenyel', characterized by its upright to outwardly spreading and uniformly mounded plant habit; freely branching habit; dense and full plant habit; uniform and freely flowering habit; small-size decorative-type inflorescences with bright yellow-colored ray florets; mid season-flowering habit; and good garden performance.

1 Drawing Sheet

Botanical designation: *Chrysanthemum×morifolium.*
Cultivar denomination: 'FIMMEVENYEL'.

BACKGROUND OF THE INVENTION

The present invention relates to a new and distinct *Chrysanthemum* plant, botanically known as *Chrysanthemum×morifolium*, commercially grown as a garden *Chrysanthemum* plant and hereinafter referred to by the name 'Fimmevenyel'.

The new *Chrysanthemum* plant is a product of a planned breeding program conducted by the Inventor in Fareham, Hampshire, United Kingdom. The objective of the breeding program is to create new mid season-flowering garden *Chrysanthemum* plants with numerous attractive inflorescences.

The new *Chrysanthemum* plant originated from a cross-pollination made in January, 2010 by the Inventor in Fareham, Hampshire, United Kingdom of a proprietary selection of *Chrysanthemum×morifolium* identified as code number 82983, not patented, as the female, or seed, parent with a proprietary selection of *Chrysanthemum×morifolium* identified as code number 82563, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2010.

Asexual reproduction of the new *Chrysanthemum* plant by terminal vegetative cuttings was first conducted in Fareham, Hampshire, United Kingdom in December, 2010. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fimmevenyel'. These characteristics in combination distinguish 'Fimmevenyel' as a new and distinct *Chrysanthemum* plant:

1. Upright to outwardly spreading and uniformly mounded plant habit.
2. Freely branching habit; dense and full plant habit.
3. Uniform and freely flowering habit.
4. Small-size decorative-type inflorescences with bright yellow-colored ray florets.
5. Mid season-flowering habit; grown under natural season conditions, plants flower in mid to late September in the United Kingdom.
6. Good garden performance.

Plants of the new *Chrysanthemum* can be compared to plants of the female parent selection. Plants of the new *Chrysanthemum* differ from plants of the female parent selection in the following characteristics:

1. Plants of the new *Chrysanthemum* have smaller inflorescences than plants of the female parent selection.

2. Plants of the new *Chrysanthemum* and the female parent selection differ in ray floret color as plants of the female parent selection have purple-colored ray florets.

Plants of the new *Chrysanthemum* can be compared to plants of the male parent selection. Plants of the new *Chrysanthemum* differ from plants of the male parent selection, in the following characteristics:

1. Grown under natural season conditions, plants of the new *Chrysanthemum* flower earlier than plants of the male parent selection.
2. Plants of the new *Chrysanthemum* and the male parent selection differ in inflorescence form as plants of the male parent selection have semi-decorative-type inflorescences.

Plants of the new *Chrysanthemum* can be compared to plants of *Chrysanthemum×morifolium* 'Sunny Yoursula', disclosed in U.S. Plant Pat. No. 16,281. In side-by-side comparisons conducted in Fareham, Hampshire, United Kingdom, plants of the new *Chrysanthemum* differed from plants of 'Sunny Yoursula' in the following characteristics:

1. Plants of the new *Chrysanthemum* had slightly smaller inflorescences than plants of 'Sunny Yoursula'.
2. Grown under natural season conditions, plants of the new *Chrysanthemum* flowered later than plants of 'Sunny Yoursula'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a top perspective view of a typical flowering plant of 'Fimmevenyel' grown in a 19-cm container during the summer and autumn in a glass-covered greenhouse in De Lier, The Netherlands. Plants were grown under natural season conditions. Plants were 3.5 months old when the photograph was taken.

DETAILED BOTANICAL DESCRIPTION

The following observations and measurements describe plants grown during the winter in 14-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were grown under long day/short night conditions for six weeks and then grown under short day/long night conditions to induce inflorescence initiation and development. Plants were twelve weeks old when the detailed description was taken. In the following description, color references are made to The Royal Horticultural Society Colour Chart, Fifth Edition, except where general terms of ordinary dictionary significance are used.

Botanical classification: *Chrysanthemum×morifolium* 'Fimmevenyel'.

Parentage:

*Female, or seed, parent*.—Proprietary selection of *Chrysanthemum×morifolium* identified as code number 82983, not patented.

*Male, or pollen, parent*.—Proprietary selection of *Chrysanthemum×morifolium* identified as code number 82563, not patented.

Propagation:

*Type*.—Terminal vegetative cuttings.

*Time to initiate roots, summer*.—About ten days at temperatures about 21° C.

*Time to initiate roots, winter*.—About twelve days at temperatures about 21° C.

*Time to produce a rooted young plant, summer*.—About three weeks at temperatures about 21° C.

*Time to produce a rooted young plant, winter*.—About four weeks at temperatures about 21° C.

*Root description*.—Fine, fibrous; light brown in color.

*Rooting habit*.—Freely branching; medium density.

Plant description:

*Plant and growth habit*.—Herbaceous decorative-type garden *Chrysanthemum*; stems upright to outwardly spreading giving a uniformly mounded appearance to the plant; numerous lateral branches and relatively short internodes, dense and full plant habit; moderately vigorous growth habit.

*Plant height*.—About 28 cm.

*Plant width*.—About 42 cm.

*Branching habit*.—Freely branching habit; about 13 lateral branches develop after removal of terminal apex (pinching).

*Lateral branches*.—Length: About 25 cm. Diameter: About 4 mm. Internode length: About 2.5 cm. Strength: Strong. Aspect: About 45° from vertical. Texture: Fine pubescence. Color: Close to 146B.

Leaf description:

*Arrangement*.—Alternate, simple.

*Length*.—About 4.2 cm.

*Width*.—About 3.3 cm.

*Shape*.—Palmately-lobed; roughly ovate with three to five lobes.

*Apex*.—Broadly mucronate to acuminate.

*Base*.—Attenuate to truncate.

*Margin*.—Palmately lobed, sinuses between lateral lobes divergent; slightly dentate.

*Texture, upper surface*.—Fine pubescence; slightly rough.

*Texture, lower surface*.—Fine pubescence; veins prominent.

*Color*.—Developing leaves, upper surface: Close to N137B. Developing leaves, lower surface: Close to 147B. Fully expanded leaves, upper surface: Close to 137A; venation, close to 146A. Fully expanded leaves, lower surface: Close to 147B; venation, close to 146B.

*Petioles*.—Length: About 1.2 cm. Diameter: About 1 mm. Texture, upper surface: Fine pubescence; slightly rough. Texture, lower surface: Fine pubescence. Color, upper surface: Close to 146A. Color, lower surface: Close to 146B.

Inflorescence description:

*Form and flowering habit*.—Decorative-type inflorescence form with ligulate-shaped ray florets; inflorescences borne on terminals above and beyond the foliar plane; disc and ray florets arranged acropetally on a capitulum; freely flowering habit with about 376 inflorescences developing per plant.

*Fragrance*.—Fragrant; pungent, herbaceous.

*Flowering response*.—Mid season-flowering habit, plants exposed to natural season conditions begin flowering in mid to late September in the United Kingdom.

*Inflorescence longevity*.—Inflorescences maintain good color and substance for about three to five weeks on the plant; inflorescences persistent.

*Inflorescence buds*.—Height: About 4 mm. Diameter: About 7 mm. Shape: Oblate. Color: Close to 147B.

*Inflorescence diameter*.—About 3.4 cm.

*Inflorescence height*.—About 8 mm.

*Receptacles*.—Height: About 2 mm. Diameter: About 3 mm. Shape: Hemispherical. Color: Close to 145A.

*Ray florets*.—Orientation: Initially upright, then about 80° from vertical. Length: About 1.3 cm. Width: About 6 mm. Shape: Ligulate. Apex: Rounded or emarginate. Base: Fused into a short tube. Margin: Entire. Texture, upper and lower surfaces: Smooth, glabrous. Number of ray florets per inflorescence: About 149 arranged in about nine whorls. Color: When opening and fully opened, upper surface: Close to 9A; color does not change with development. When opening and fully opened, lower surface: Close to 9B; color does not change with development.

*Disc florets*.—Disc floret development has not been observed on plants of the new *Chrysanthemum*.

*Phyllaries*.—Number of phyllaries per inflorescence: About 26 arranged in about three whorls. Length: About 6 mm. Width: About 3 mm. Shape: Lanceolate. Apex: Rounded. Base: Rounded. Margin: Entire. Texture, upper surface: Smooth, glabrous; waxy. Texture, lower surface: Fine pubescence; waxy. Color, upper surface: Close to 137C. Color, lower surface: Close to 137B.

*Peduncles*.—Length, terminal peduncle: About 1 cm. Diameter, terminal peduncle: About 2 mm. Angle: About 45° from vertical. Strength: Moderately strong; flexible. Texture: Fine pubescence. Color: Close to 138A.

*Reproductive organs*.—Androecium: None observed. Gynoecium: Pistil length: About 4 mm. Stigma shape: Bi-parted. Stigma color: Close to 1B. Style length: About 3 mm. Style color: Close to 7A. Ovary color: Close to 155C.

*Seeds and fruits*.—Seed and fruit production has not been observed on plants of the new *Chrysanthemum*.

Disease & pest resistance: Resistance to pathogens and pests common to *Chrysanthemum* plants has not been observed on plants of the new *Chrysanthemum*.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fimmevenyel' as illustrated and described.

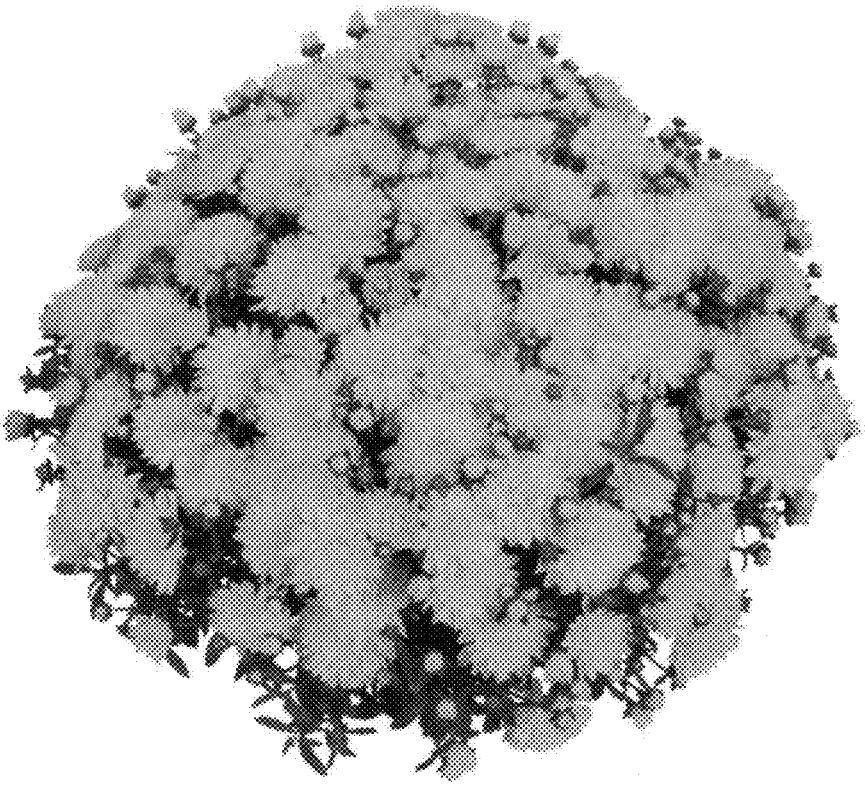

* * * * *